United States Patent [19]
Johnson et al.

[11] Patent Number: 5,674,846
[45] Date of Patent: Oct. 7, 1997

[54] INSECTICIDAL PEPTIDES FROM SEGESTRIA SP. SPIDER VENOM

[75] Inventors: Janice H. Johnson; Robert M. Kral, Jr., both of Salt Lake City, Utah

[73] Assignee: NPS Pharmaceuticals, Inc., Salt Lake City, Utah

[21] Appl. No.: 706,278

[22] Filed: Sep. 4, 1996

[51] Int. Cl.$^6$ .......................... A01N 37/18; C07K 14/435
[52] U.S. Cl. .......................... 514/12; 530/350; 530/300; 530/858
[58] Field of Search .......................... 530/300, 350, 530/858; 514/2, 12; 536/23.5; 435/69.1

[56] References Cited

U.S. PATENT DOCUMENTS

| | | | |
|---|---|---|---|
| 4,925,664 | 5/1990 | Jackson et al. | 424/537 |
| 5,037,846 | 8/1991 | Saccomano et al. | 514/419 |
| 5,177,308 | 1/1993 | Barton et al. | 800/205 |
| 5,185,369 | 2/1993 | Saccomano et al. | 514/502 |
| 5,227,397 | 7/1993 | Saccomano et al. | 514/419 |

FOREIGN PATENT DOCUMENTS

| | | |
|---|---|---|
| 2005658 | 6/1990 | Canada. |
| 9423540 | 11/1994 | United Kingdom. |
| 9501074 | 1/1995 | United Kingdom. |
| 9513293 | 6/1995 | United Kingdom. |
| WO93/18145 | 9/1993 | WIPO. |
| WO96/16171 | 5/1996 | WIPO. |

OTHER PUBLICATIONS

Sagdiev et al. "Study of venom toxic components of the cellular spider *Segestria florentina*". Bioorg. Khim: 13(8): 1013–1018 1987.
Sagdiev et al. "Purification and characterization of a neurotoxin from the venom of the spider *Segestria florentina*". Dokl. Akad. Nauk SSSR 282(2): 463–465. 1985.
Newcomb et al. "SNX–325, a novel calcium antagonist from the spider *Segestria florentina*" Biochemistry 34(26): 8341–8347 1995.
Tashmukhamedov et al. "Neuroactive spider venoms". Stud. Neurosci (Simpler Ner. Syst) 13:21–33 1991.
"Overproduction of Encapsulated Insecticidal Crystal Proteins in a *Bacillus thuringiensis* spoOA Mutant", Lereclus et al., *Bio/Technology*, vol. 13, Jan. 13, 1995, p. 67.
"Insecticidal Activity of Spider (Araneae), Centipede (Chilopoda), Scorpion (Scorpionida), and Snake (Serpentes) Venoms", Quistad et al., *Journal of Economic Entomology*, vol. 85, No. 1, Feb. 1992, pp. 33–39.

"Development of a Recombinant Baculovirus Expressing an Insect–Selective Neurotoxin: Potential for Pest Control", McCutchen et al., *Bio/Technology*, vol. 9, Sep. 1991, pp. 848–852.
"Identification of Insecticidal Peptides from Venom of the Trap–Door Spider, *Aptostichus schlingeri* (Ctenizidae)", Skinner et al., *Toxicon*, vol. 30, No. 9, 1992, pp. 1043–1050.
"Neurotoxins from Venoms of the Hymenoptera–Twenty––Five Years of Research in Amsterdam", Tom Piek, *Comp. Biochem. Physiol.*, vol. 96C, No. 2, 1990, pp. 223–233.
"Curatoxins, Neurotoxic Insecticidal Polypeptides Isolated From the Funnel–Web Spider *Hololena Curta*", Stapleton et al., *The Journal of Biological Chemistry*, vol. 265, No. 4, Feb. 5, 1990, pp. 2054–2059.
"Perspectives in Biochemistry", Lila M. Gierasch, *American Chemical Society*, vol. 28, No. 3, Feb. 7, 1989, pp. 923–030.
"Purification and Characterization of Two Classes of Neurotoxins from the Funnel Web Spider, *Agelenopsis aperta*", Skinner et al., *The Journal of Biological Chemistry*, vol. 264, No. 4, Feb. 5, 1989, pp. 2150–2155.
"Trends in the Development of Baculovirus Expression Vectors", Luckow et al., *Bio/Technology*, vol. 6, Jan. 1988, pp. 47–55.
"The Action of a Toxin From the Venom of the Wasp Habrobracon Hebetor (SAY) on the Neuromuscular Transmission of Insects" Slavnova et al., Institute For Bioorganic Chemistry, Apr. 16, 1987, pp. 1–3.
"Characterization of Two Paralysing Proteins Toxins (A–MTX and B–MTX), Isolated from a Homogenate of the Wasp *Microbracon Hebetor* (SAY)", Visser et al., *Comp. Biochem. Physiol.*, vol. 75B, No. 3, 1983, pp. 523–530.
"Two Different Paralysing Preparations Obtained from a Homogenate of the Wasp *Microbracon Hebetor* (SAY)", Spanjer et al., *Toxicon*, vol. 15, pp. 413–421.
"Isolation and Some Biochemical Properties of a Paralysing Toxin from the Venom of the Wasp *Microbracon Hebetor* (SAY)" Visser et al., *Toxicon*, vol. 14, 1976, pp. 357–370.
"Short Communication Stability of *Microbracon Hebetor* (SAY) Venom Preparations", D. Drenth, *Toxicon*, vol. 12, pp. 541–542.

*Primary Examiner*—Robert A. Wax
*Assistant Examiner*—Gabriele E. Bugalsky
*Attorney, Agent, or Firm*—Madson & Metcalf

[57] ABSTRACT

This invention relates to an insecticidally effective peptide isolated from the spider, Segestria sp., characterized by its paralytic effect on insect pests and low mammalian toxicity. This invention also discloses methods for producing recombinant peptides, as well as methods of utilizing these peptides as insecticidal agents.

5 Claims, 1 Drawing Sheet

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 31
        ( B ) TYPE: amino acid
        ( C ) STRANDEDNESS: single
        ( D ) TOPOLOGY: unkown ( i i ) MOLECULE TYPE:
        ( A ) DESCRIPTION: peptide ( i v ) ANTI-SENSE: no ( v i ) ORIGINAL SOURCE:
        ( A ) ORGANISM: Segestria sp.
        ( C ) INDIVIDUAL ISOLATE: peptide A
        ( I ) ORGANELLE: Venom glands ( x i ) SEQUENCE DESCRIPTION: SEQ ID NO:1:

```
Lys Glu Xaa Lys Pro Asp Gly Glu Gln Xaa Gly Ile Thr Asp His
 1               5                      10                    15

Asn Asp Xaa Xaa Asn Ala Xaa Val Xaa Pro Asp Gly Pro Phe Met
                 20                  25                    30

Arg
 31
```

INSECTICIDAL PEPTIDES FROM SEGESTRIA SP. SPIDER VENOM

FIELD OF THE INVENTION

The present invention is related to a peptide isolated from spider venom which displays insecticidal characteristics. More particularly, the present invention relates to an insecticidally effective peptide that is isolated from the spider Segestria sp. and characterized by its paralytic effect on specific insect pests.

BACKGROUND OF THE INVENTION

Insects are among humankind's most serious competitors for food and fiber resources. Approximately one third of worldwide agricultural production is lost to insect damage each year. Insects such as termites and carpenter ants cause millions of dollars in structural damage every year. Many serious human and animal diseases, including malaria, yellow fever, sleeping sickness, viral encephalitis, and plague, are transmitted by insects. Efforts to control insect pests have resulted in the development of a global insecticide industry with annual sales of approximately $6 billion. Most of these products are synthetic chemical neurotoxins such as chlorinated hydrocarbons (e.g., DDT), carbamates (e.g., carbaryl), organophosphates (e.g., malathion), and synthetic pyrethroids (e.g., cypermethrin). Relatively minor, though significant, chemical insecticides include insect growth regulators (e.g., diflubenzuron and methoprene) and metabolic disrupters (e.g., hydroxymethylnon).

Synthetic chemical insecticides are effective for controlling pest insects in a wide variety of agricultural, urban, and public health situations. Unfortunately there are significant, often severe, side effects associated with the use of these products. Many pest populations have developed significant resistance to virtually all chemical insecticides, requiring higher and higher rates of usage for continued control. In a number of severe cases, highly resistant pest populations have developed which cannot be controlled by any available product. Chemical insecticides may also have deleterious effects on non-target organisms. Populations of beneficial arthropods, such as predators and parasites, are sometimes more severely affected by chemical applications than the pests themselves. Minor pests, ordinarily held in check by these beneficial organisms, may become serious pests when their natural constraints are removed by the use of chemical insecticides. Thus, new pest problems may be created by attempts to solve established problems.

Chemical insecticides may also have adverse effects on vertebrates. The use of DDT has been banned in the United States, due primarily to the insecticide's great environmental persistence and its resulting tendency to accumulate in the tissues of predatory birds, thereby disrupting their ability to produce viable eggs. The use of carbofuran has been severely restricted due to its avian toxicity, and many species of fish are known to be quite sensitive to a variety of insecticides. A number of insecticides, such as methyl parathion, are also quite toxic to humans and other mammals, and by accident or misuse have caused a number of human poisonings. Clearly, the field of insect control would benefit greatly from the discovery of insecticides with improved selectivity for insects and reduced effects on non-target organisms.

The problems described above, along with other concerns including the possibility that some insecticides may act as human carcinogens, have created a strong demand for the development of safer methods of insect control. The practice of integrated pest management (IPM), which seeks to minimize the adverse environmental effects of chemical insecticides by relying on cultural and biological methods, is one response to this demand. The success of IPM, however, has been less than hoped due to the lack of effective biological alternatives to chemical insecticides. Because these alternatives can reduce the frequency and severity of pest outbreaks and delay the development of insecticide-resistant pest populations, their availability is critical to the success of IPM programs.

Insect pathogens have been the objects of much study as potential pest control agents. Generally, these pathogens are quite selective for insects and in many cases affect only a few closely related species of insects. A number of insect pathogens have been developed as products, including bacteria (e.g., *Bacillus thuringiensis* and *Bacillus popiliae*), viruses (e.g., nuclear polyhedrosis viruses) and protozoa (e.g., the microsporidian *Nosema locustae*). These products occupy only a small fraction of the insecticide market, however, due largely to their relatively slow action. Although pathogens may ultimately cause a high level of mortality in pest populations, the insects may take weeks to die and continue to feed for much of that time. Thus, an unacceptably high level of crop or commodity damage may be inflicted before control is achieved. Currently, researchers are actively seeking ways to improve the effectiveness of insect pathogens and other biological control tools.

Insecticidal toxins from arthropods have been the objects of increasing interest over the past decade. These materials have proved useful for the detailed study of neural and neuromuscular physiology in insects. They have also been used to enhance the effectiveness of certain insect pathogens. The insecticidal toxin AaIT, from the scorpion *Androctonus australis*, has been employed for both purposes. This toxin belongs to a group of peptides that are lethal to a variety of insects but have no detectable effect in mammals, even though they come from a species known to be dangerous to humans. Other toxins in *A. australis* venom are lethal to mammals but have no effect on insects. This selectivity is particularly interesting in view of the fact that both groups of toxins act on voltage-sensitive sodium channels. Understanding the molecular basis of this selectivity may lead to the development of chemical insecticides with reduced effects on mammals and other non-target organisms.

The effectiveness of insect pathogens has also been enhanced by the use of genes encoding AaIT and other insect-selective toxins. A number of reports have demonstrated that the insecticidal properties of the *Autographa californica* nuclear polyhedrosis virus (AcMNPV), a member of the baculovirus family, can be enhanced by modifying the viral genome to include a gene encoding an insecticidal toxin. Toxins employed for this purpose include AaIT, TxP-1 from the parasitic mite *Pyemotes tritici*, DTX9.2 from the spider *Diguetia canities*, and NPS-326 (now known as TaITX-1) from the spider *Tegenaria agrestis*. These toxins were inserted into the AcMNPV genome under the control of either the p10 promoter or the polyhedrin promoter. Both promoters regulate the high-level expression of very late viral genes encoding component proteins of the viral occlusion bodies. In every case, recombinant viruses containing a toxin gene were more effective than the wild type virus, as measured by the time required for infected insects to die or become moribund.

Because the baculovirus system is well known to be a highly efficient and flexible method of expressing biologically active proteins from many different sources, it is reasonable to expect that newly discovered toxins will also be useful for enhancing the insecticidal activity of these viruses.

The use of these toxins is not expected to be limited to baculoviruses, however. Many other microbes, including bacteria and fungi, are known to be susceptible to such genetic manipulation. Certain bacteria and fungi, in fact, are widely used for large-scale production of exogenous proteins from humans and other mammalian sources; other insect viruses have also been studied as potential expression vectors. Examples of such pathogens include the entomopoxviruses, the bacterium *Escherichia coli*, and the fungus *Pichia pastoris*. Such pathogens may be enhanced as pest control agents by their modification to include toxin genes, much as the efficacy of baculoviruses has been enhanced by such modifications.

Thus it is clear that insecticidal toxins from arthropods may be used to advance the field of insect control in a number of significant ways. A novel composition of matter having the desired properties of insecticidal efficacy and insect selectivity, therefore, is expected to be useful in the art whether or not it can be used directly as an insecticidal compound. The means by which such a composition of matter may be made useful are well known to those skilled in the art, and are characterized by (but not limited to) the examples provided in the preceding paragraphs.

Thus, it is apparent that it would be a significant advancement in the art to discover novel biological insect control agents that do not pose the environmental and health risks associated with chemical insecticides. It would be a further advancement in the art to provide insect control agents that were selective for insects and that did not adversely affect humans or other animal or plant life. In that regard, it would be a significant advancement in the art to provide methods and compositions for controlling insects using naturally occurring insecticidal peptides.

SUMMARY OF THE INVENTION

The present invention relates to an insecticidally effective protein isolated from the spider, Segestria sp., and characterized by its paralytic effect on insects pests. This protein is exemplified herein by the peptide SEQ ID NO:1 (also at times designated herein as "peptide A"). The characteristics of this peptide are more fully set forth below. When small quantities of this protein are administered by injection into the abdomen of larvae of the tobacco budworm, the larvae are incapacitated by an excitatory paralysis.

This invention also relates to methods for modifying and improving the described peptide for use as an insecticidal agent. A signal sequence and propeptide sequence, for example, may be useful for efficiently secreting the Segestria peptide or targeting it to a specific cell or location in a cell. Signal sequences could, therefore, obviate the need for lengthy purification procedures and enhance the secretion and insecticidal efficacy of the Segestria peptide.

Finally, this invention relates to the use of this peptide as an agent for combating insect pests. Large quantities of this peptide may be obtained using known recombinant technology methods. DNA sequences that code for the peptide can be engineered into an expression vector, and the protein may then be expressed in either a prokaryotic host, such as *E. coli*, or a eukaryotic host, such as the insect cell line Sf9. The isolated protein may then be applied directly to the plant or animal sought to be protected from insect pests. The isolated protein may also be used to characterize the pharmacology of its target site by use in receptor binding assays, neurophysiological assays, or other appropriate test systems.

Alternatively, nucleic acid sequences that code for the peptide may be engineered into a natural pathogen of insects such as Bacillus or baculovirus. The recombinant pathogens can be utilized to transfer nucleic acids encoding the peptide directly into the insect pests. These recombinantly engineered pathogens will likely have significantly increased insecticidal efficacy in comparison with the parental wild-type pathogens.

These and other objects and advantages of the invention will become apparent upon reading the following detailed description and appended claims, and upon reference to the accompanying drawing.

DETAILED DESCRIPTION OF THE DRAWING

Figure 1:
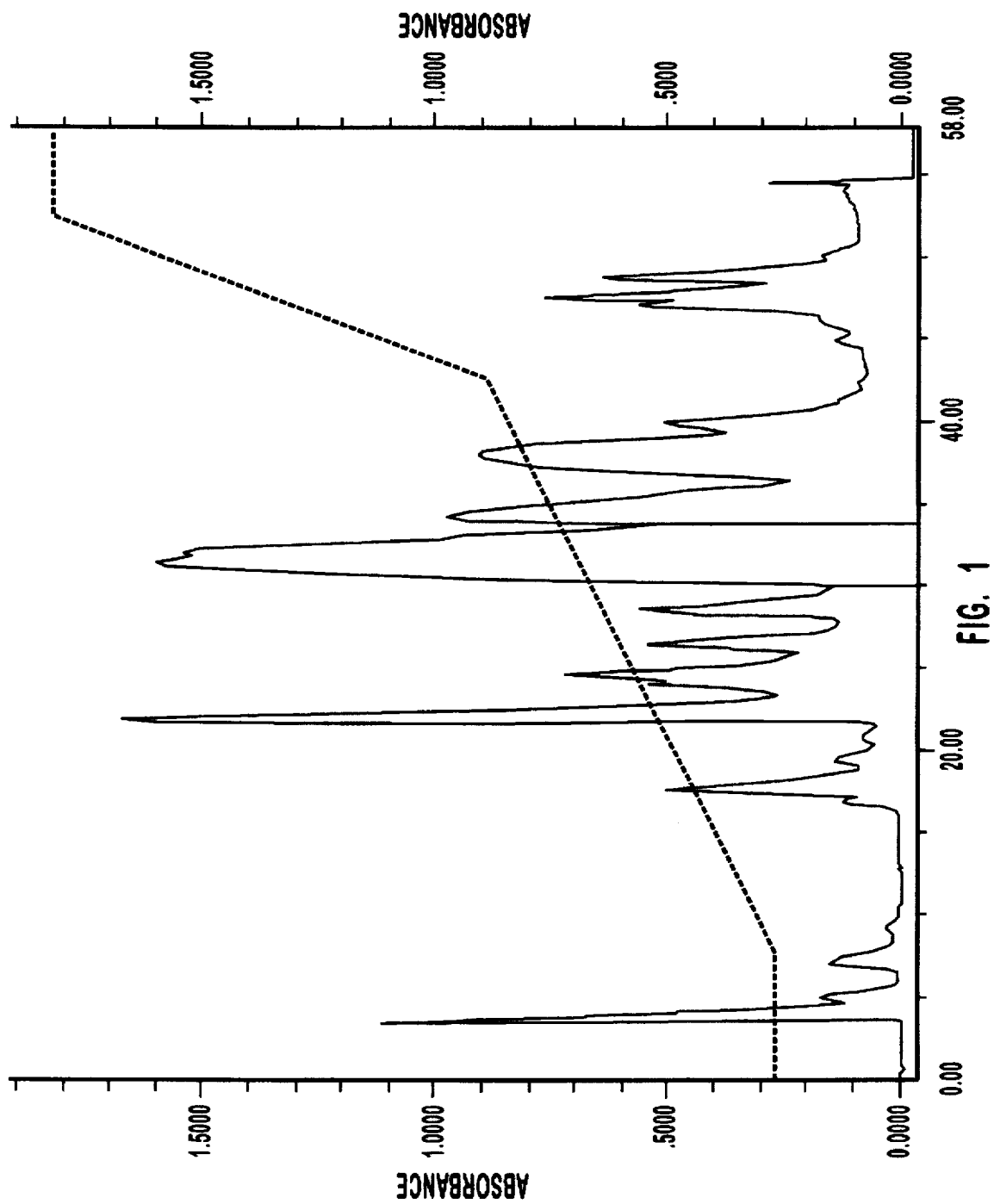

FIG. 1 is a chromatogram illustrating the results of fractionating whole Segestria venom by reversed-phase chromatography. The peptide SEQ ID NO:1 (peptide A) eluted between 30-34 minutes.

DETAILED DESCRIPTION OF THE INVENTION

As discussed above, the present invention relates to a peptide isolated from spider venom which displays insecticidal characteristics. More particularly, the present invention relates to an insecticidally effective peptide that is isolated from the spider, Segestria sp., and is characterized by its paralytic effect on selected insect pests. For the purposes of this application, the term "insecticidally effective" shall be defined as effective in incapacitating by excitatory paralysis the larvae of the tobacco budworm (*H. virescens*) under the conditions set forth herein.

As mentioned above, this protein is exemplified herein by the peptide SEQ ID NO:1 (peptide A). The specification describes how this peptide may be expressed by recombinant DNA methods. In addition, it is possible, by known techniques, to transform or transfect expression vectors containing a toxin cDNA sequence into a host cell or organism.

Accordingly, the present invention provides a naturally occurring peptide for use as an insecticide. The naturally occurring peptide may be used in a variety of ways to control insects, or to study the effects of the peptide on insects.

EXPERIMENTAL METHODS AND CHARACTERIZATION

The primary operative techniques and terms used in this specification are well known in the art. Nevertheless, in order to provide a clear understanding of the full scope of the present invention, reference is made to the following experimental methods and characterization techniques that may be used to practice the invention.

VENOM PRODUCTION

Spiders were collected from known wild populations in central California and identified as Segestria sp. (family Segestridae). Venom was collected by an electrical milking technique that avoids contamination of the venom with digestive enzymes and other regurgitated substances.

BIOASSAY

Whole venom was isolated by known techniques from the spider, Segestria. The whole venom, or peptides purified therefrom, were dissolved in sterile buffered physiological saline. For testing and characterization purposes, venom and toxins were administered by injection into the abdomen of fifth instar larvae of the tobacco budworm (TBW), *Heliothis virescens*. Control larvae were injected with an equal volume of saline. After treatment, the insects were placed individually in Petri dishes, with food, and observed.

Insects that could not right themselves within thirty seconds of being placed on their backs or side were considered paralyzed. Fifty percent paralytic dose ($PD_{50}$) values were calculated by probit regression (see Example 1). Raymond, *Ser. Ent. med et Parasitol*, 22, 117-121 (1985).

PROTEIN PURIFICATION

A peptide from Segestria spider venom was isolated using methods known in the art. Briefly, whole venom was first fractionated by reversed-phase chromatography. Fractions were collected by monitoring ultraviolet absorbance. Based on biological activity, one peak was identified as containing the peptide of interest.

This biologically active fraction was further purified by cation-exchange chromatography. Fractions again were collected by monitoring UV absorbance and were bioassayed. The biologically active fraction from the cation-exchange chromatography was then chromatographed by neutral reversed-phase chromatography.

The bioactive fraction from the neutral reversed-phase column was desalted by reversed-phase chromatography. The resulting fraction contained substantially pure peptide SEQ ID NO:1 (peptide A). The observed molecular mass for purified peptide SEQ ID NO:1 (peptide A) is 10203.7.

ANTIBODIES

Included within the scope of this invention are antibodies directed towards the peptide SEQ ID NO:1 (peptide A) and, by extension, to similar peptides. Antibodies are proteins that are generated in animals and said to recognize or bind to a specific molecule, such as a peptide. When studying the insect toxin of this invention, it would be useful to be able to monitor the toxin's quantity, location and association with other proteins. Techniques such as Western blots, immunoprecipitation assays, and immunohistochemical assays cannot be performed without employing an antibody that specifically recognizes the peptide of interest.

In addition, antibodies can be used, by methods well known in the art, to purify and subsequently clone the proteins to which this toxin binds. This may be done by screening expression libraries, for example. Alternatively, the venom protein may be purified by immobilizing the antibody to a solid support and by employing immunoaffinity chromatography.

Antibodies can be produced by a variety of methods well known in the art. Generally, antibodies are generated by immunizing a foreign animal (typically, rabbits or mice) with purified proteins. Insect toxins that are purified from whole spider venom, recombinantly expressed, or synthesized would be suitable for antibody production. The proteins induce an immune response in the animal, resulting in the production of many antibodies that recognize the protein. The sera of these animals contain polyclonal antibodies, which are a mixture of many antibodies that recognize the protein or a fragment or derivative thereof.

Alternatively, a single antibody, referred to as a monoclonal antibody, may be produced by hybridoma cloning technology well known in the art. See, Kennett, et al., *Monoclonal Antibodies, Hybridomas: A New Dimension in Biological Analyses*, Plenum Press, New York (1982). Briefly, the animal is immunized and the splenocytes of the animals are isolated and immortalized by fusing them with a suitable myeloma cell line. The cells are cloned by limiting dilution. The cell lines that produce suitable monoclonal antibodies may be propagated indefinitely.

Thus, it is possible to produce antibodies to the peptide of this invention in order to facilitate further characterization, research, and development related to the use of the insecticidal toxin of interest.

cDNA ISOLATION AND CHARACTERIZATION

Included within the scope of this invention is a cDNA coding for the Segestria toxin. The cDNA may be isolated by methods well known to those in the art. Generally, the N-terminal sequence of peptide SEQ ID NO:1 (peptide A) was determined by chemical sequencing. Based on the genetic code and available codon usage data for spiders, degenerate oligonucleotides complementary to the toxin gene's nucleic acid sequence may be synthesized. Such degenerate oligonucleotides may be used to isolate a cDNA coding for the toxin by methods well known to those in the art. See, e.g., Sambrook et al., *Molecular Cloning : A Laboratory Manual*, 2d ed. Cold Spring Harbor Press (1989). Briefly, messenger RNA (mRNA) isolated from the spiders or, preferably, from the spiders' venom glands, could be used as a template for the synthesis of cDNA by a process known as "reverse transcription." The cDNA corresponding to the toxin gene may be isolated from the total collection of cDNAs in at least one of two ways, both of which are well known to those in the art. First, the collection of cDNAs may be cloned into an appropriate vector such as a plasmid or bacteriophage vector. Vectors carrying the toxin gene cDNA may be identified and isolated using the degenerate oligonucleotides as "probes." This process, well known to those in the art, is referred to as "screening a library." Alternatively, the degenerate oligonucleotides may be used to selectively amplify the toxin gene in a process known as the "polymerase chain reaction" (PCR). The isolated toxin gene cDNA may be characterized (e.g., by DNA sequencing) or manipulated (e.g., used to express recombinant protein).

PROTEIN MODIFICATIONS

Protein modifications can be subdivided into four general categories: chemical processing, additions, substitutions and deletions. These general groups apply to both the nucleic acid and amino acid sequences of the protein. While protein modifications may occur naturally, most often protein modifications are deliberately engineered into the nucleic acid sequence that codes for the protein. Protein modification techniques such as site-directed mutagenesis are well known in the art and in many cases are commercially available as kits complete with instructions from, for example, Amersham and Bethesda Research Laboratories.

Chemical processing generally occurs after protein translation, and includes modifications such as amidation, glycosylation, palmitoylation, and isomerization. Such processing events may be necessary for the stability and optimal activity of toxins. Heck et al., *Science*, 266: 1065-1068 (1994).

A protein modification may occur through an addition. Additions as defined herein are modifications made to the nucleic acid or amino acid sequence which produce a protein containing at least one amino acid more than the primary amino acid sequence of the native protein without significant alterations of function. Naturally occurring nucleic acid additions in the coding region of the protein often severely impair the protein's function by causing a shift in the reading frame. From the point of the nucleotide addition, the amino acid sequence of the encoded protein is entirely different from the primary amino acid sequence of the native protein. It is possible, however, to have an addition within the coding region of the protein that does not change the reading frame of the protein. Nucleotide additions in the 5' or 3' untranslated region of the gene usually do not affect protein function.

As mentioned above, additions are usually deliberately engineered into the protein. The addition of a methionine to the amino terminus of the mature protein, as well as additions of other amino acids and nucleotides which facilitate the expression of the protein such as stop codons and ribosomal binding sites are included within the scope of this invention.

It is also understood that the addition of a signal sequence or signal peptide is included within the scope of this invention. Signal sequences direct protein transport to a particular location within the cell or organism. Alternatively, signal sequences may cause the protein to be secreted.

Comparison of all known signal peptides reveals that they are approximately 15–30 residues in length. Within the signal peptide there is a 7–13 residue stretch that constitutes a hydrophobic region (h-region). The h-region is rich in Ala, Met, Val, Ile, Phe and Trp, and occasionally contains Pro, Gly, Ser or Thr residues. von Heijne, G., *J. Mol. Biol.* 184, 99–105 (1983). This sequence homology is shared from bacteria to higher eukaryotes, suggesting that the localization machinery is highly conserved. Proteins from one organism can be translocated and correctly processed by the localization machinery of several other organisms. Mueller et al., *J. Biol. Chem.*, 257, 11860–11863 (1982). Conversely, recombinant proteins comprising a signal peptide from one organism and a protein from a different organism are also properly localized. Jabbar & Nayak, *Mol. Cell. Biol.*, 7, 1476–1485 (1987). Studies suggest that signal sequences form their functional conformation independent of the remaining protein sequence, which explains why signal sequences are readily interchangeable between different proteins and different species. In fact, studies performed using the gene coding for the scorpion peptide, AaIT, in baculovirus demonstrate that the addition of a signal sequence from one species to an insect toxin from another species is likely to succeed. The AaIT peptide was fused with the signal sequence from bombyxin, a secretory peptide from the silkworm *Bombyx mori*, and shown to secrete a functional AaIT peptide that was toxic to insects. McCutchen et al., *Bio/Technology*, 9, 848–852 (1991).

Finally, a secretory signal peptide may also greatly facilitate the purification of a peptide in an expression system by having the protein product secreted into the culture media rather than being retained by the host cell. In many instances the proteins are sufficiently pure in the media such that further purification is not required. This is particularly true for small proteins which are stable under a broad range of conditions.

Signal peptides for many prokaryotes, as well as eukaryotes and viruses are well characterized and documented in the literature. Thus, using basic recombinant DNA technology, such as PCR or synthetic oligonucleotides, a recombinant protein containing a signal peptide at its amino terminus can be easily engineered.

It is also understood that the addition of an antigenic epitope is included within the scope of the present invention. An epitope is a small, usually 6–20 amino acid residues, antigenic peptide for which a unique and specific antibody exists. Thus, by recombinantly engineering an antigenic epitope, the scientist is guaranteed a specific and effective antibody that will recognize the specific peptide. One such antigenic epitope is the c-myc epitope which has been recombinantly engineered into many proteins without any deleterious effect on function. Several other epitopes have been well documented in the literature and are commercially available along with the antibodies that recognize them.

Like the signal peptides, a recombinant protein containing an epitope can be engineered using common recombinant DNA technology. Unlike the signal peptide, however, the antigenic epitope may be engineered at the amino terminus or the carboxy terminus of the protein.

Protein modifications that occur through substitutions are also included within the scope of the invention. Substitutions as defined herein are modifications made to the nucleic acid or amino acid sequence of the protein, producing a protein with an amino acid sequence different from the amino acid sequence of the primary protein, without significantly altering the function of the toxin. Like additions, substitutions may be natural or artificial. It is well known in the art that amino acid substitutions may be made without significantly altering the protein's function. This is particularly true when the modification is conservative, i.e. the substitution of an amino acid with characteristics similar to those of the original. Conservative substitutions involve the use of natural or synthetic amino acids which because of size, charge, polarity and conformation can be substituted for the amino acid in question without significantly affecting the structure and function of the protein. Frequently, amino acids may be replaced by similar amino acids without deleteriously affecting the protein's function.

Whether a specific amino acid residue can be replaced at all, or whether it can only be replaced by a similar amino acid, is best determined by comparing the specific peptide of interest with related toxins. Residues that are absolutely conserved, i.e. that are identical in all the members of a protein family usually cannot be replaced. This is often the case with cysteine residues, which are critical for the formation of the protein's secondary structure. Residues that are highly conserved (i.e. they are present in most but not all members of the family) can usually be replaced by other similar amino acids without significantly affecting the protein's function. Finally, amino acids that are not conserved within a family can usually be freely replaced.

In general, the non-polar amino acids Gly, Ala, Val, Ile and Leu; the non-polar aromatic amino acids Phe, Trp and Tyr; the neutral polar amino acids Ser, Thr, Cys, Gln, Asn and Met; the basic amino acids Lys, Arg and His; and the acidic amino acids Asp and Glu represent groups of similar amino acids. This list is not exhaustive. For example, it is well known that Ala, Gly, Ser and sometimes Cys can substitute for each other even though they belong to different groups.

Conservative amino acid substitutions are not limited to naturally occurring amino acids but may also include substitutions by synthetic amino acids. Commonly used synthetic amino acids are ω amino acids of various chain lengths and cyclohexyl alanine which are neutral non-polar analogs; citulline and methionine sulfoxide which are neutral non-polar analogs, phenylglycine which is an aromatic neutral analog; cysteic acid which is an acidic amino acid analog and ornithine which is a basic amino acid analog. Like the naturally occurring amino acids, this list is not exhaustive, but merely exemplary of the substitutions that are well known in the art.

Finally, protein modifications may occur through deletions. Deletions as defined herein are modifications made to the nucleic acid or amino acid sequence of the protein which produce a protein containing at least one amino acid less than the primary amino acid sequence of the native protein. Like additions, naturally occurring deletions within the coding region of the protein usually severely impair the function of the protein, while deletions in the 5' and 3' untranslated region do not affect the function of the protein.

Deliberate deletions, however, may be required or useful for the expression of the protein in a foreign organism. For example, in the spider, the toxin's leader sequence is most likely removed by proteolysis as the prepropeptide is secreted. A deletion that removes the leader sequence from the precursor protein will, therefore, yield a functional mature protein similar to that secreted by the spider.

RECOMBINANT EXPRESSION

Once the cDNA has been recombinantly modified to express a protein suited for a particular need, the cDNA, including all modifications, is subcloned into an expression vector. In general, expression vectors are like plasmids which additionally contain a promoter, a termination signal and sometimes a selectable marker. Any expression vector containing a prokaryotic, eukaryotic or viral promoter and a termination signal is included within the scope of the invention.

A promoter is a nucleic acid sequence, generally engineered 5' to the cDNA, which recruits and directs the transcription of RNA using the cDNA as a template. From this transcribed RNA message, the cell can assemble the protein that is encoded by the cDNA through a process known as translation.

Promoters can generally be classified as constitutive, inducible, or tissue specific. A constitutive promoter is a promoter which is not regulated to a significant extent by any cellular factors and continually directs the transcription of the RNA. These promoters are used when large quantities of protein are desired. The cytomegalovirus promoter and the Rous Sarcoma virus promoters are examples of constitutive eukaryotic promoters. The int promoter of bacteriophage 1 and the bla promoter of β-lactamase are examples of constitutive prokaryotic promoters.

Included in this group are promoters that are characterized as early or late promoters. These promoters are usually viral promoters, which are activated to high levels either early or late in viral replication. The baculovirus p10 and polyhedrin promoters are examples of late promoters.

Inducible promoters are promoters that are induced or repressed by certain factors. Inducible promoters allow regulation of the amount of protein produced, and the timing of such production. Examples of inducible promoters are the eukaryotic metallothionine promoter, which is induced by increased levels of heavy metals, and the prokaryotic lacZ promoter, which is induced in response to isopropyl β-D-thiogalacto-pyranoside (IPTG).

Finally, tissue specific promoters are promoters that only function in a particular cell type. These promoters are typically used when expression of the protein in all cell types would be harmful to the organism. An example of a mammalian tissue specific promoter is the skeletal muscle creatine kinase promoter.

An expression vector also requires a termination signal. The termination signal is usually engineered 3' to the protein-coding sequence of interest. In higher eukaryotes, for example, the expression vector must contain a polyadenylation signal in order for the transcript to be translated into a protein. A termination signal like the adenovirus polyadenylation signal and the baculovirus polyhedrin polyadenylation signal may be used. Alternatively, a peptide's own polyadenylation signal may serve as an efficient termination signal.

In most instances, the expression vector also requires a selectable marker which allows for the identification of cells which have actively incorporated the expression vector. These selectable markers are genes whose protein products confer resistance to antibiotics or other chemicals. Thus, cells that are capable of growing in the presence or absence of a certain chemical are known to contain the expression vector. Examples of selectable markers are the β-lactamase gene, which confers resistance to ampicillin in prokaryotes, and the neomycin gene, which confers resistance to G-418 in eukaryotic cells. An expression vector is not limited to one selectable marker and, in fact, most expression vectors contain multiple selectable markers.

In short, the availability and knowledge of prokaryotic and eukaryotic promoters, termination signals and selectable markers is well known in the art. In fact, many types of expression vectors for bacterial, yeast, mammalian and viral expression systems are commercially available.

RECOMBINANT HOSTS

The desired expression vector, including the cDNA, is then transformed or transfected into the host cell or organism. Both transformation and transfection refer to the incorporation of the expression vector into a host by methods such as electroporation or calcium phosphate treatment, which are well known in the art. Like plasmids, expression vectors may remain episomal or be incorporated as part of the host's genome. Incorporation into the host genome can be accomplished by either random integration or homologous recombination. Random integration results in the insertion of multiple copies of the gene into unknown locations of the host's genome, while homologous recombination results in the insertion of one copy of the gene in a known location of the host's genome. The above techniques are expected to be useful for the expression of the peptide of this invention and are included within the scope of the invention.

Recombinant hosts are chosen based on the goals to be achieved. For the purposes of expressing an insecticidally effective protein there are two general types of hosts which are particularly useful: hosts for producing large quantities of recombinant proteins and hosts for infecting insect pests.

Bacteria, particularly *E. coli*, are still the most commonly used host for the production of large quantities of recombinant proteins. A recombinant bacterial host expressing an insect toxin, therefore, is expected to be a useful technique for producing the insect toxin of the present invention for use as insecticides. The toxin may be fused to a signal peptide as described above or expressed as a mature protein. Bacterial overexpression systems are well known in the art and are commercially available.

The toxin expressed in a bacterial overexpression system, however, will not contain post-translational modifications. Therefore, baculovirus infected insects or insect cell lines are frequently employed to produce large quantities of post-translationally modified proteins. A wide variety of prokaryotic and eukaryotic proteins have been successfully expressed in baculovirus. Luckow and Summers, *Bio/Technology*, 6, 47–55 (1988); Summers and Smith, *Texas Agricultural Experimental Station Bulletin*, 1555, 1–56 (1987).

As in bacterial hosts, recombinant baculoviruses may express proteins as either fusion or mature proteins. Expression of foreign genes has been known to yield as much as 500 mg/liter of protein. Because insect cells are eukaryotic, the recombinant proteins produced using baculovirus infected insect cells are very similar to the native proteins. Studies have shown that recombinant proteins expressed by a baculovirus vector may be secreted, localized to the nucleus, localized to the cell surface, disulfide-linked, proteolytically cleaved, phosphorylated, N-glycosylated, O-glycosylated, myristylated, or palmitylated. Luckow and Summers, *Bio/Technology*, 6, 47–55 (1988).

The recombinant peptide isolated from these hosts may be applied directly to the plants or animals sought to be protected from the insect pests. As discussed later, the recombinant virus itself may be used as a pest control agent.

Alternatively, the recombinant peptide will be used to study the physiological mechanism which leads to the paralysis of insect pests. Given the mechanism of action of other spider toxins, it is likely that the peptide of interest disclosed herein acts by altering the function of neurons, possibly by modifying the function of certain ion channels. Moreover, the art strongly suggests that this toxin is highly selective for insect pests, while displaying negligible mammalian toxicity. This is true despite the fact that analogous ion channels and other target sites are abundantly present in mammals. Some of these targets, notably voltage-sensitive sodium channels, are important targets for chemical insecticides. Therefore, peptides, such as the toxin of this invention, may be used to help elucidate and characterize the differences between the insect and vertebrate forms of these target sites. This information can then be used in chemical design studies aimed at developing chemical insecticides that are highly selective for insect pests. Pathogens infecting insects represent a second class of recombinant hosts useful for the expression of the subject peptides. From an agricultural standpoint, bacteria and baculoviruses are the most promising pathogen candidates, although pathogenic fungi might also be used for this purpose.

Certain bacteria pathogenic to insects, especially *Bacillus thuringiensis* (B.t.), have been used to control a variety of insect pests. Unfortunately, naturally occurring pathogens often have limited utility as biological insecticides due to limitations in delivery, toxicity and speed of action. Current work, however, has demonstrated that *B.t.* may be engineered to produce a recombinant bacterium that overcomes some of the limitations of the wild-type *B.t.* Most notably, the *B.t.* delta-endotoxin gene has been engineered into bacterial pathogens to produce hybrid hosts which display superior insecticidal properties. Similarly, the production of recombinantly engineered bacterial or fungal pathogens that express the toxin of this invention are thought to be useful and thus are included within the scope of the invention.

Wild-type baculoviruses are also natural regulators of many different types of insects pests, including *Heliothis virescens* (tobacco budworm), *Orgyia pseudotsugata* (Douglas fir tussock moth) and *Laspeyresia pomonella* (codling moth). See Gröner, 1986, "Specificity and Safety of Baculovirus", in *Biological Properties and Molecular Biology*, Vol I, Granados and Federici, eds., CRC Press, Inc., Boca Raton, Fla. (1986). Baculoviruses, such as *Autographa californica* nuclear polyhedrosis virus, produce post-infection viral progeny; extracellular viral particles and occluded viral particles. The occluded viral particles are important because they provide a means for horizontal and vertical transmission. After infected insect pests die, millions of viral particles are left behind protected by the viral occlusion bodies. Thus, when insect pests feed on contaminated plants, they ingest the occlusion bodies. The occlusion bodies dissolve in the alkaline environment of the insect gut, releasing the viral particles, which infect and replicate in the insect's midgut tissue. Secondary infection within a host is spread by extracellular, non-occluded viral particles.

Unfortunately, insects infected by baculoviruses may take a week or more to die and continue to feed for much of that time, making the commercial use of wild-type baculovirus economically infeasible. It has been shown, however, that baculoviruses, such as the *Autographa californica* nuclear polyhedrosis virus, can be recombinantly engineered to express an insecticidal toxin, thus accelerating their pathogenic effects. McCutchen, et al., *Bio/Technology*, 9, 848–852 (1991); Tomalski et al., *Nature*, 352, 82–85 (1991); Stewart et al., *Nature*, 352, 85–88 (1991); Krapcho et al., Insecticidally Effective Peptides, U.S. Pat. No. 5,441,934 (Aug. 15, 1995); Krapcho et al., Insecticidally Effective Peptides, U.S. Pat. No. 5,461,032 (Oct. 23, 1995) patents (FMC/NPS). A recombinant vector, Pacuw2(B).AaIT, was constructed containing a polyhedrin gene driven by the polyhedrin promoter and the AaIT insect toxin driven by the p10 promoter. The resulting recombinant baculovirus was orally infective under normal conditions. Furthermore, the AaIT toxin was secreted in the course of infection and caused paralysis of both *Manduca sexta* larvae, an unnatural host for the virus, and *Heliothis virescens* larvae, a natural host.

Using basic recombinant technology well known in the art, it is expected that DNA sequences coding for the peptide of the present invention could similarly be recombinantly engineered to produce a recombinant baculovirus which would display increased host range and toxicity.

Recombinant baculoviruses expressing the toxins of this invention, like current insecticides, could then be administered to crops that are to be protected from insect pests. The release of recombinant baculoviruses into the environment is expected to be a safe and effective means of controlling insect pests. First, naturally occurring insecticidal peptides are highly selective. In addition, baculoviruses do not infect mammals and are highly selective within an insect group. Therefore, by carefully selecting the baculovirus host and insecticidal peptide, it is possible to engineer recombinant baculoviruses that are highly selective for the target insect pest and have negligible effects on non-targeted organisms, including beneficial insects. Second, recombinant baculoviruses are likely to be at a competitive disadvantage relative to wild type viruses. Polyhedrin-negative viruses, for example, cannot form their own occlusion bodies, and therefore have greatly reduced persistence under field conditions. Thus, the relatively short life of the recombinant baculoviruses further reduces the potential environmental consequences of their use.

The quantity and frequency of recombinant baculovirus application will necessarily depend on such things as the particular crop being protected, the insect pest, and the climate. Accordingly, the quantity and frequency of recombinant baculovirus application is best determined empirically.

EXAMPLES

The following examples are given to illustrate various embodiments which have been made or may be made in accordance with the present invention. These examples are given by way of example only, and it is to be understood that the following examples are not comprehensive or exhaustive.

Example 1

Bioassays: Whole venom from a spider, Segestria sp. (family Segestridae), was dissolved in the desired volume of sterile, buffered physiological saline. Samples were administered by injection into the abdomen of the fifth instar larvae of the tobacco budworm, *Heliothis virescens*, as previously described. Control larvae were injected with equal volumes of saline.

Whole Segestria venom caused a distinctive paralytic effect in *H. virescens* larvae. The $PD_{50}$ (50% paralytic dose) of peptide A by injection into *H. virescens* larvae was 4.9 μg/g (95% confidence interval 2.7–8.9 μg/g), and the $PD_{90}$ was 10.0 μg/g (95% confidence interval 6.3–61.2 μg/g). At high doses ($PD_{90}$ and greater), larvae were visibly affected within five minutes of toxin injection. These initial effects included tremors and spasms of the body wall musculature. Within 15 minutes of injection, these symptoms gave way to a distinctive rigid paralysis. At this point, the body wall muscles were so rigid that the larvae could be lightly grasped at the midpoint of the body, with finely pointed forceps, and held in the air with no visible sagging of the body. This rigid stage persisted for only a short time; within two hours of injection, paralyzed larvae became quite flaccid. Paralyzed larvae generally did not recover, although in a few cases recovery did occur. This progression of symptoms was consistently observed in numerous assays with Segestria venom, venom fractions, and purified samples of peptide A.

Example 2

Purification of Peptide SEQ ID NO:1 (peptide A): Whole Segestria venom was fractionated by reversed-phase chromatography. The whole venom (250 microliters (µl)) was diluted with 3 ml of 15% acetonitrile/water constant in 0.1% TFA and the sample was chromatographed in three aliquots on a Vydac C-18 column (300 Å, 10×250 mm) equilibrated in the same buffer. Eight minutes after injection of the sample the column was developed with a 35 minute linear gradient from 15–50% acetonitrile/water constant in 0.1% TFA, followed by a 10 minute linear gradient to 100% acetonitrile/water constant in 0.1% TFA. The results are illustrated in FIG. 1. The flow rate was 3.5 ml/minute and the effluent was monitored at 220 nm. Fractions were collected manually. Like fractions from different runs were pooled and lyophilized. SEQ ID NO:1 (peptide A) eluted between 30–34 minutes. A small portion of the pooled, lyophilized fraction was used to confirm biological activity; the remaining material was dissolved in 3 ml of 50 mM sodium acetate, pH 4.5 and fractionated by cation-exchange chromatography.

Cation-exchange chromatography was performed on a HEMA-IEC BIO SB column (10 µm, 4.6×150 mm, from Alltech Associates, Deerfield, Ill. 60015). The solution containing SEQ ID NO:1 (peptide A) from the reversed-phase chromatography was divided in half. Each half was loaded onto the HEMA-IEC BIO SB column equilibrated 50 mM sodium acetate, pH 4.5. After 5 minutes, the column was developed with a 30 minute linear gradient from 0–0.3M NaCl in 50 mM sodium acetate buffer, pH 4.5, followed by a 10 minute linear gradient from 0.3–1M NaCl in 50 mM sodium acetate buffer, pH 4.5. Elution was at 1 ml/minute and the effluent was monitored at 280 nm. In both chromatographies, the biologically active material was the major component eluting between 15 and 18 minutes. These biologically active fractions were pooled for further purification.

The pooled bioactive material from the cation-exchange chromatography was chromatographed on a Vydac C-18 reversed-phase column (300 Å, 10×250 mm) equilibrated in 20% acetonitrile/50 mM $NaH_2PO_4$, pH 7.0. After 5 minutes, the column was developed with a 44 minute linear gradient from 20–42% acetonitrile/50 mM $NaH_2PO_4$, pH 7.0, followed by a 5 minute linear gradient from 42–70% acetonitrile/50 mM $NaH_2PO_4$, pH 7.0. Elution was at 3.5 ml/minute and the effluent was monitored at 220 nm. Two peaks were observed, one eluting between 39 and 41 minutes and the other peak eluting between 41 and 43 minutes. Only the later eluting peak was bioactive.

The bioactive fraction from the neutral reversed-phase column was desalted by reversed-phase chromatography on a Vydac C-18 reversed-phase column (300 Å, 10×250 mm) equilibrated in 25% acetonitrile/water constant in 0.1% TFA. After 5 minutes, the column was developed with a 64 minute linear gradient from 25–57% acetonitrile/water constant in 0.1% TFA, followed by a 5 minute linear gradient from 57–100% acetonitrile/water constant in 0.1% TFA. Elution was at 3.5 ml/minute and the effluent was monitored at 220 nm. The major peak, eluting between 24–27 minutes, was found to contain the biological activity.

The observed mass of the purified peptide, SEQ ID NO:1 (peptide A), as determined by Mass Assisted Laser Desorption Time of Flight mass spectrometry (MALDI TOF) as obtained by Molecular Ion, Torrance, Calif. was 10203.7±0.1%. The $PD_{50}$ of peptide SEQ ID NO:1 (peptide A) in TBW larvae was 4.9 µg/g with the 95% confidence interval ranging from 2.7 to 8.9 µg/g.

Example 3

N-terminal Amino Acid Sequencing of Peptide SEQ ID NO:1 (peptide A): A partial N-terminal amino acid sequence analysis of the underivatized SEQ ID NO:1 (peptide A) peptide was performed at the Biotechnology Center at Utah State University. The sequence is shown below:

Lys Glu Xaa Lys Pro Asp Gly Glu Gln Xaa Gly Ile Thr Asp His Asn Asp Xaa Xaa Asn Ala Xaa Val Xaa Pro Asp Gly Pro Phe Met Arg (where Xaa represents an unknown amino acid residue).

Example 4

Mammalian toxicity of Segestria toxins: Peptide A was tested for mammalian toxicity by intracerebroventricular (i.c.v.) injection in mice. Three male Swiss-Webster mice (average body mass ~21 grams) were injected with peptide A. At a dose of 20 micrograms per mouse (~1 mg/kg), peptide A had no effect. These results indicate that insecticidal peptide A may have considerable selectivity for insects.

SUMMARY

The present invention relates to an insecticidally effective protein isolated from the spider, Segestria, characterized by its paralytic effect on insect pests. When small, insecticidally effective, quantities of this protein are administered to selected insects, the insects are paralyzed or killed.

As described above, the present invention also relates to the cloning of these peptides using routine recombinant DNA technology. The present invention also provides methods for modifying and improving the described peptide for use as insecticidal agents. In addition, the present invention relates to the use of these proteins as agents for combating insect pests. Large quantities of these peptides may be obtained using known recombinant technology methods. DNA sequences that code for the peptide can be engineered into an expression vector, which is then inserted into either a prokaryotic host, such as *E. coli*, or a eukaryotic host, such as insect cells. The isolated protein may then be applied directly to the plant or animal sought to be protected from insect pests.

As an alternative, the peptide may be engineered into a natural pathogen of insects such as Bacillus or baculovirus as described above. Such recombinant pathogens can be utilized to transfer the peptide directly into the insect pests. These recombinantly engineered pathogens will likely have significantly enhanced insecticidal properties.

The invention may be embodied in other specific forms without departing from its essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

What is claimed is:

1. A Segestria spider venom fraction which has a paralytic effect on *Heliothis virescens* comprising a protein comprising SEQ ID NO:1.

2. A substantially purified, insecticidally effective protein isolated from Segestria spider venom, which has a paralytic effect on insect pests, wherein the protein comprises SEQ ID NO:1.

3. A substantially purified, insecticidally effective protein isolated from Segestria spider venom, which has a paralytic effect on insect pests, wherein the protein further has an observed molecular mass of about 10200 amu, and a $PD_{50}$ *Heliothis virescens* of approximately 4.9 µg/g.

4. A method of controlling insects comprising exposing insects to an insecticidally effective quantity of the protein of claim 3.

5. A method of controlling insects comprising exposing insects to an insecticidally effective quantity of a protein comprising the amino acid sequence of SEQ ID NO:1.

* * * * *